United States Patent
De Vries et al.

(10) Patent No.: US 9,676,120 B2
(45) Date of Patent: Jun. 13, 2017

(54) MIXING DEVICE FOR BONE CEMENT AND METHOD FOR MIXING BONE CEMENT

(75) Inventors: Jan Albert De Vries, HH Zelhem (NL); Wout R. Loman, AH Almen (NL)

(73) Assignee: APP BIOMATERIALS GMBH, Dieburg (DE)

( * ) Notice: Subject to any disclaimer, the term of this patent is extended or adjusted under 35 U.S.C. 154(b) by 1166 days.

(21) Appl. No.: 13/521,585

(22) PCT Filed: Jan. 11, 2011

(86) PCT No.: PCT/EP2011/000066
§ 371 (c)(1),
(2), (4) Date: May 16, 2013

(87) PCT Pub. No.: WO2011/083095
PCT Pub. Date: Jul. 14, 2011

(65) Prior Publication Data
US 2013/0223181 A1    Aug. 29, 2013

(30) Foreign Application Priority Data
Jan. 11, 2010  (DE) .................. 10 2010 004 342

(51) Int. Cl.
*B01F 13/06*  (2006.01)
*B29B 7/24*  (2006.01)
(Continued)

(52) U.S. Cl.
CPC ............ *B29B 7/24* (2013.01); *A61B 17/8827* (2013.01); *B01F 11/0082* (2013.01);
(Continued)

(58) Field of Classification Search
CPC ........................................................ B01F 13/06
(Continued)

(56) References Cited

U.S. PATENT DOCUMENTS 3,009,686 A     11/1961  Kaplan
3,144,966 A  *  8/1964   Cook .................. B01F 7/00208
                                                    156/500

(Continued)

FOREIGN PATENT DOCUMENTS

DE         4243587      10/1993
DE         19532015     3/1997
(Continued)

OTHER PUBLICATIONS

German Office Action dated Jul. 23, 2014 corresponding to German Patent Application No. DE 10 2010 004 342.7 with English translation, 8 Pages.

(Continued)

*Primary Examiner* — David Sorkin
(74) *Attorney, Agent, or Firm* — Ohlandt, Greeley, Ruggiero & Perle, L.L.P.

(57) ABSTRACT

A mixing device for bone cement is provided. The mixing device includes a mixing handle, an housing, and a mixing paddle. The mixing handle having a rod, where at least portions of the rod are in tubular form with monomer inside of the rod. The housing has a mixing chamber in which the monomer and a powder are miscible. The mixing paddle is arranged in the mixing chamber and is movable via the rod.

9 Claims, 7 Drawing Sheets

(51) Int. Cl.
*A61B 17/88* (2006.01)
*B01F 11/00* (2006.01)
*B01F 13/00* (2006.01)
*B01F 15/02* (2006.01)
*A61F 2/46* (2006.01)

(52) U.S. Cl.
CPC ........ *B01F 13/002* (2013.01); *B01F 13/0023* (2013.01); *B01F 15/0205* (2013.01); *B01F 15/0206* (2013.01); *B01F 15/0224* (2013.01); *A61F 2002/4685* (2013.01)

(58) Field of Classification Search
USPC ................................ 366/130, 139, 189, 332
See application file for complete search history.

(56) References Cited

U.S. PATENT DOCUMENTS

| | | | |
|---|---|---|---|
| 5,114,240 A | 5/1992 | Kindt-Larsen | |
| 5,779,356 A * | 7/1998 | Chan | A61B 17/8827 366/139 |
| 5,857,772 A | 1/1999 | Washington | |
| 7,018,089 B2 * | 3/2006 | Wenz | A61M 5/31511 206/219 |
| 7,073,936 B1 * | 7/2006 | Jonsson | B01F 15/0226 366/139 |
| 2003/0155381 A1 | 8/2003 | Chan | |
| 2010/0046315 A1 * | 2/2010 | Merkhan | A61B 17/8825 366/8 |

FOREIGN PATENT DOCUMENTS

| | | |
|---|---|---|
| DE | 10 2007 041 666 | 4/2009 |
| GB | 2338428 A | 12/1999 |
| WO | 99/22854 | 5/1999 |
| WO | 2007/000631 | 1/2007 |

OTHER PUBLICATIONS

International Search Report dated Mar. 17, 2011 corresponding to International Patent Application No. PCT/EP2011/000066.
Written Opinion dated Mar. 17, 2011 corresponding to International Patent Application No. PCT/EP2011/000066.
English Translation of International Preliminary Report on Patentability dated Jul. 26, 2012 corresponding to International Patent Application No. PCT/EP2011/000066.

* cited by examiner

MIXING DEVICE FOR BONE CEMENT AND METHOD FOR MIXING BONE CEMENT

FIELD OF THE INVENTION

The invention relates to a mixing device for bone cement and to a method for producing bone cement.

BACKGROUND OF THE INVENTION

Mixing devices for bone cement are known. One of such mixing devices is shown, for example, in applicant's German patent application DE 10 2007 041 666 A1.

When mixing bone cement, a powder, in particular an acrylate, is mixed with a liquid monomer. After mixing the components a crosslinking reaction occurs during which the bone cement progressively solidifies. The mixed, but not yet solidified bone cement is applied for example into medullary canals in which then a prosthesis is implanted. To prevent bubbles from being formed or to prevent harmful gases from being released into the environment, vacuum-mixing systems are known, in which a vacuum hose is attached to the mixing vessel.

A drawback of such known vacuum mixing systems is that a pump is required to generate the vacuum. Moreover, when mixing bone cement there are stringent requirements for sterility. A disadvantage of known mixing systems is that air enters into the mixing vessel already during mixing.

Also, in many cases known bone cement mixing systems are inconvenient to use, and due to the necessary variety of procedure steps for mixing there is a risk that the user makes a mistake, in particular that the ratio between the monomer and the bone cement powder is not correctly adjusted.

OBJECT OF THE INVENTION

Therefore, an object of the invention is to provide a bone cement mixing device that is easy to operate.

Another object of the invention is to reduce the risk of contamination of the bone cement during the mixing process.

SUMMARY OF THE INVENTION

The object of the invention is already achieved by a mixing device for bone cement and by a method for mixing bone cement according to any of the independent claims.

Preferred embodiments and refinements of the invention are described in the respective dependent claims.

The invention provides a mixing device for bone cement comprising a housing with a mixing chamber in which the monomer and the powder can be mixed. The mixing chamber is formed as a cylinder, and a vacuum can be generated by means of a piston that is movable within the cylinder.

Thus, for the purposes of the invention the vacuum is generated directly in the mixing chamber, and therefore no vacuum pump is required. Providing the mixing chamber in form of a cylinder in which the piston is moved, permits a particularly simple construction of such a mixing device with only few parts, which is preferably designed as a disposable mixing device.

It will be understood that the term vacuum does not only mean a pressure of almost 0 bar, but also a negative pressure.

In a preferred embodiment of the invention, the stroke of the piston is dimensioned such that a predefined residual pressure from 50 to 300 mbar, preferably from 100 to 150 mbar, is generated. This may be facilitated for example by a defined void volume, which is not evacuated through the movement of the piston. The predefined residual pressure prevents gas bubbles from being formed in the monomer due to reaching the boiling point by the pressure reduction.

Cylinder and piston may have almost any cross-section. In particular a circular cross section is suggested.

Preferably, the piston is operable manually so that a drive motor may be dispensed with.

According to one embodiment of the invention, the piston may be moved in the mixing chamber by means of a threaded spindle.

In particular, a threaded spindle is provided which includes a threaded rod connected to the piston, the rod being engaged by a rotary handle which is arranged adjacent to the mixing chamber. The rotary handle is rotatably mounted to the housing of the mixing device and has a threaded nut corresponding to the threaded rod. The threaded nut may be formed in a very simple manner, when using suitable plastics a plastic slot alone is sufficient which corresponds to the flanks of the thread of the threaded rod. Thus, when the user rotates the rotary handle in the predetermined sense of rotation, the rotational movement is converted into a linear movement thereby retracting the piston and generating a vacuum in the sealed mixing chamber. The vacuum prevents gases from escaping and improves the blending of the components in the mixing chamber.

Through the pitch of the thread of the threaded rod, the transmission ratio between the rotational movement and the linear movement may be defined. So on the one hand the maximum torque may be defined via the pitch of the threaded rod, and on the other the number of rotations required. A pitch from 0.5 to 4 cm, more preferably from 1.5 to 2.5 cm has proven to be particularly suitable. Thus, the threaded rod has a fairly large pitch, permitting to move the piston to its end position with only a few rotations.

It is also conceivable to provide the housing of the mixing chamber in form of a threaded spindle. In particular, the threads may be provided on the outside of a cylindrical housing.

In an alternative embodiment of the invention, the piston may be moved via a preloaded spring. For example, the piston may be biased by a spring, and the user unlocks an unlocking means which releases the spring. In this manner, the vacuum may be generated with a single action. A disadvantage of this embodiment, however, is the somewhat higher cost and the fact that the piston cannot be moved in the opposite direction by the same mechanism.

In one embodiment of the invention, a movable mixing paddle is arranged on the side of the housing opposite to the piston head. Thus, in this embodiment of the invention, a mixing paddle is arranged on one side of the preferably cylindrical housing, and the piston on the other side.

In one preferred embodiment of the invention, the mixing paddle is connected to a manipulation handle via a rod guided in the housing. Using the manipulation handle, the mixing paddle may be moved back and forth and/or rotated in the cylindrical mixing chamber and so mix the components of the bone cement.

In a refinement of the invention, at least portions of the rod are formed as a tube that is connected to the mixing chamber and the rod has at least one predetermined breaking point.

In this way, the rod by means of which the mixing paddle is moved may be used as some kind of a transfer hose. To this end, the handle is severed from the remaining rod at the predetermined breaking point, and thus an opening is exposed.

In one refinement of the invention, the rod comprises at least two predetermined breaking points spaced from each other. This allows to provide a transfer hose which can be adjusted to at least two different lengths, depending on where the rod is broken apart. Depending on the particular use of the bone cement, the transfer hose may thus be adjusted to an optimum length.

In order to provide a particularly sterile and easy to operate application system, in one preferred embodiment of the invention, the mixing chamber is already pre-filled with bone cement powder.

In a particularly preferred embodiment of the invention, the mixing device is pre-filled both with bone cement and with a monomer, and is sealed hermetically.

Thus, the invention allows to provide a mixing device which is completely sealed until application (for example until breaking off the rod described above). So the risk of contamination from the ambient air is reduced considerably. At the same time the risk of incorrectly adjusting the ratio of bone cement powder to monomer is eliminated.

In a modification of the invention, the piston for generating the vacuum is adapted to be movable in a second direction, for pressing out the bone cement. Preferably, the movement of the piston in the second direction is accomplished via the same rotary handle which was used to generate the vacuum. Thus, after mixing the bone cement the piston which was previously used to produce the vacuum can be used for pressing out the bone cement from the mixing chamber.

With such an embodiment it is not necessary to connect the mixing device to another component such as a pistol for pressing out a mixing device which is in form of a cartridge.

In another embodiment of the invention, the mixing chamber has a scale, so that the user may recognize, how much bone cement he/she has applied.

The invention further relates to a mixing device for bone cement, in particular a mixing device with one or more of the features described above.

The mixing device comprises a housing with a mixing chamber in which a monomer and a powder can be mixed, and a mixing paddle is arranged in the mixing chamber, which mixing paddle is movable via a rod guided in the housing.

The rod, at least in portions thereof, is formed as a tube to be used as a type of transfer hose after mixing the bone cement.

According to the invention, the monomer is arranged in the rod. The volume of the rod may thus be used for storing the monomer. The handling of the mixing device is greatly improved, since it is already pre-filled with the required amount of monomer. Moreover, a very sterile construction of the mixing device is ensured.

In a refinement of the invention, the monomer is arranged in a monomer container which is introduced into the tubular portion of the rod.

Thus, it is easily possible to use a material for the separate monomer container, which is permanently resistant to the monomer. In particular, a plastic material provided with a diffusion barrier layer, or a metal, especially aluminum, are suggested.

In particular, the monomer may be arranged in an insertion hose that is inserted into the rod. This may be an elongated bag of flexible material, in particular of a film having a diffusion barrier layer.

Likewise, the monomer container may comprise aluminum foil, in particular as part of a multilayer composite.

In one modification of the invention, the rod for moving the mixing paddle has a manipulation handle and a predetermined breaking point, and the monomer container is removable from the rod after the manipulation handle has been broken off.

In particular, it is suggested that the monomer container is designed as some kind of a small tube which is connected to the manipulation handle without having a corresponding predetermined breaking point. After breaking off the handle, the emptied monomer container is pulled out from the tubular portion of the rod with the manipulation handle. So when applying the bone cement the components of the monomer container which otherwise might hinder the exit of the viscous bone cement are no longer in the way.

In a refinement of the invention, means for perforating the monomer container are arranged in the mixing chamber.

In particular it is suggested to provide a spike at the head of an opposed piston. So, when initially depressing the mixing paddle the spike contacts the end face of the monomer container, and the monomer container is cut or perforated by the spike so that the monomer is released.

In a preferred embodiment of the invention, the monomer container is partially filled with a gas, in particular with air. So the monomer container may be completely sealed, and after opening the monomer container the monomer is displaced from the monomer container due to the expansion of the gas volume. By suitably adjusting the gas volume and the negative pressure prevailing in the mixing chamber prior to mixing, the expansion of the gas due to the pressure difference alone is sufficient. Alternatively or in combination, a propellant may be added to the monomer.

The invention further relates to a method for mixing bone cement, in particular by means of a mixing device described above.

First, a vacuum is generated by means of a piston guided in the mixing chamber.

By manipulating a mixing paddle via a rod that is guided in the housing of the mixing device, a monomer container arranged at or inside the rod is perforated or cut upon initial actuation, and the monomer enters into a mixing chamber filled with bone cement powder.

By further manipulating the mixing paddle via a manipulation handle coupled with the rod, the bone cement is mixed.

When the bone cement has been mixed, the manipulation handle is broken off, whereby a tubular portion of the rod exposes a channel to the outside.

Then, the piston is moved in the opposite direction, whereby the bone cement exits through the tubular portion of the rod.

The method allows to mix bone cement in a particularly simple manner with just a few steps. Moreover, the method may be performed in a hermetically sealed mixing device, so that the bone cement only comes into contact with the ambient air when the rod is broken off.

Preferably, the mixing paddle is moved into an uppermost position before breaking off the manipulation handle, so that when pressing out the bone cement the latter does not has to be pressed past the mixing paddle.

In one refinement of the invention, the monomer is displaced from the monomer container by a gas volume provided in the monomer container.

Preferably, the monomer container after being emptied is pulled out of the rod together with the broken off manipulation handle.

BRIEF DESCRIPTION OF THE DRAWINGS

The invention will now be described in detail with reference to exemplary embodiments schematically illustrated in FIGS. 1 through 9, wherein.

DETAILED DESCRIPTION OF THE DRAWINGS

Figure 1:
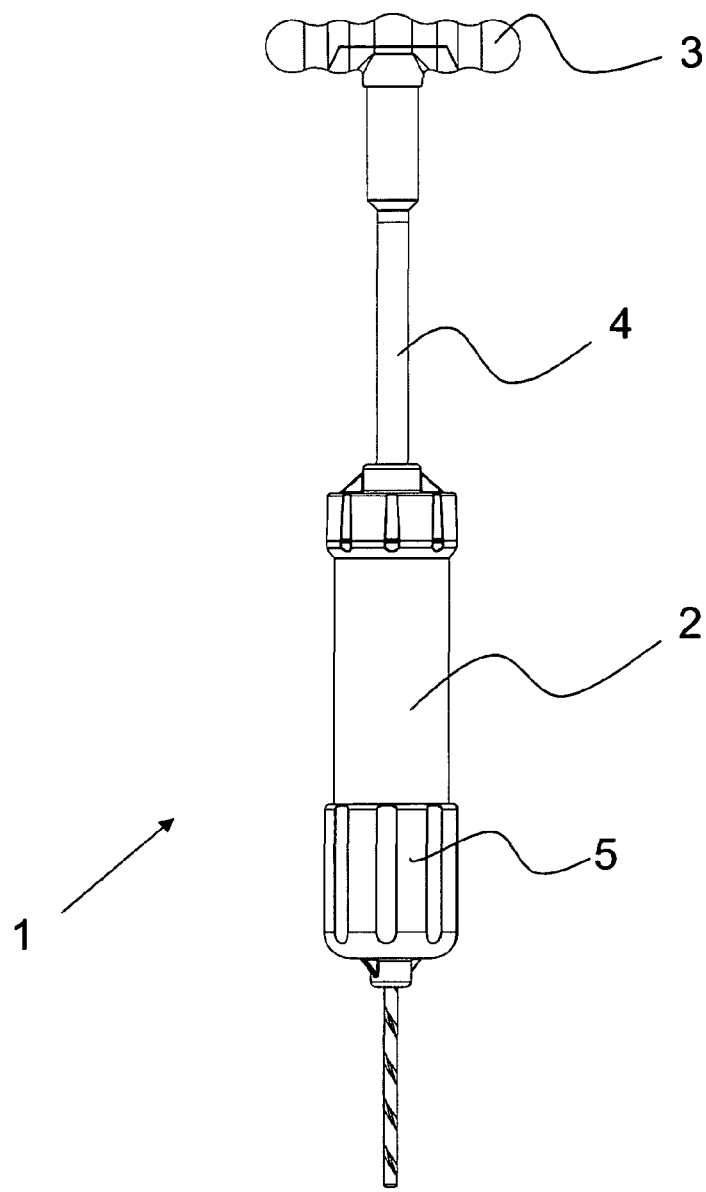
FIG. 1 is a schematic view of a mixing device.

Referring to FIG. 1, the essential components of a bone cement mixing device 1 will be described in detail with reference to a schematically illustrated exemplary embodiment.

Mixing device 1 comprises a substantially cylindrically shaped housing 2 which includes the mixing chamber for mixing the bone cement (not shown).

On the upper side a manipulation handle 3 can be seen which is connected to a mixing paddle (not shown) via a rod 4 which is guided in housing 2.

On the lower side, a rotary handle 5 is arranged.

For mixing and applying the bone cement, the user (not shown) first rotates rotary handle 5, in this embodiment in counter-clockwise direction. Upon reaching an end position of rotary handle 5, the user, via manipulation handle 3, manipulates the mixing paddle and moves it from top to bottom in order to mix the bone cement. Upon initial actuation, the monomer container (not shown) is opened automatically, so that the bone cement is mixed by further movement of manipulation handle 3.

Then the user breaks off manipulation handle 3.

The remaining portion of rod 4 is formed as some type of a tube or transfer hose.

Then the user turns handle 5 in the opposite direction, and the bone cement exits rod 4 and can be applied.

Figure 2:
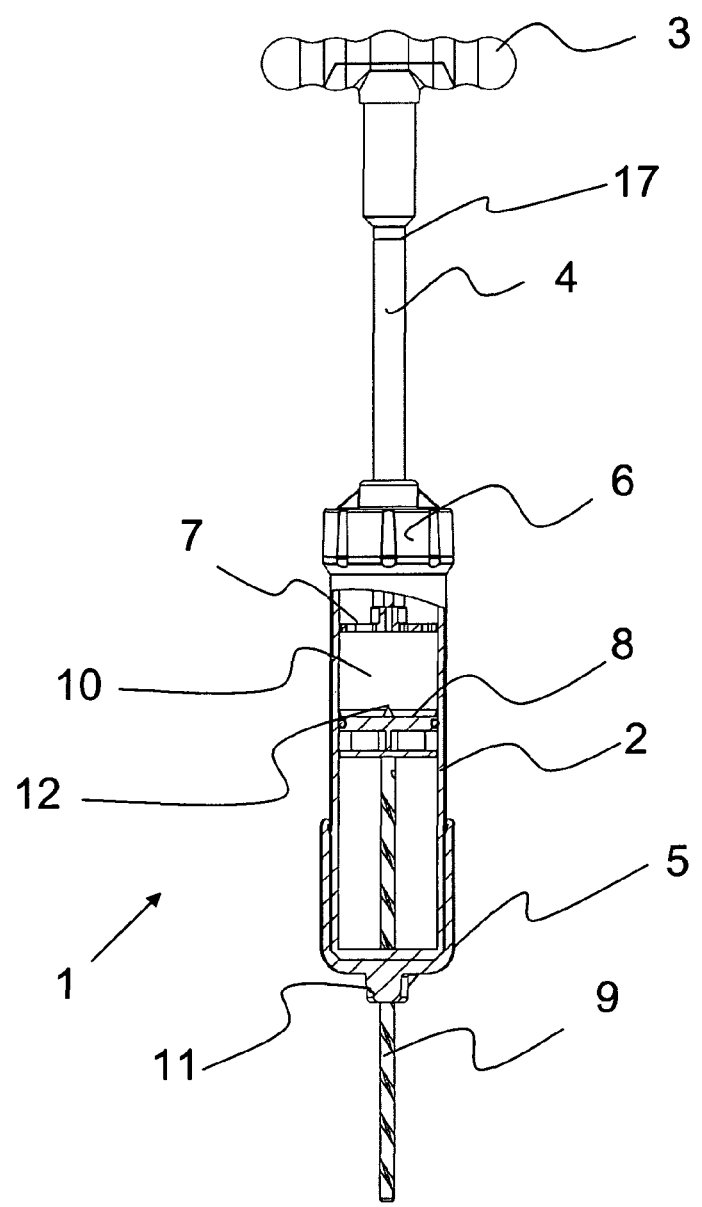
FIG. 2 is a partially cutaway view of the mixing device illustrated in FIG. 1.

FIG. 2 shows a partially cutaway view of the mixing device illustrated in FIG. 1. In particular the mixing chamber 10 can be seen, which may be pre-filled with bone cement powder (not shown). Mixing chamber 10 is formed as a cylinder in which a piston 8 is guided which is connected to a threaded rod 9.

Rotary handle 5 is rotatably mounted to housing 2. In this exemplary embodiment, rotary handle 5 encloses the lower portion of the housing, whereby a particularly large gripping surface can be provided while virtually maintaining the dimensions.

At its lower side rotary handle 5 comprises a spindle nut which cooperates with threaded rod 9. Rotary handle 5 and threaded rod 9 thus form a threaded spindle by means of which the rotational movement of rotary handle 5 is convertible into a translational movement of the threaded rod and thus of piston 8.

By retracting piston 8, first a vacuum can be produced in mixing chamber 10.

Opposite the piston, on the other side of housing 2, a mixing paddle 7 is guided by means of rod 4, which mixing paddle may be moved up and down by means of manipulation handle 3. When mixing paddle 7 is actuated for a first time mixing paddle 7 abuts against piston 8 which is equipped with a spike 12.

Spike 12 which is disposed at the head of piston 8 thereby opens a container (not shown) which is filled with the monomer and disposed inside rod 4, whereby the monomer enters mixing chamber 10.

By further manipulating mixing paddle 7, the bone cement powder and monomer are mixed to form bone cement.

Subsequently, the user completely pulls up manipulation handle 3 and breaks off manipulation handle 3 at predetermined breaking point 17 provided on the rod. Rod 4 is formed as a tube, at least up to predetermined breaking point 17, and is used as a transfer hose when manipulation handle 3 has been broken off.

By rotating rotary handle 5 in the opposite direction, piston 8 moves upwardly and drives the mixed bone cement upwards, through the tubular portion of rod 4.

Figure 3:
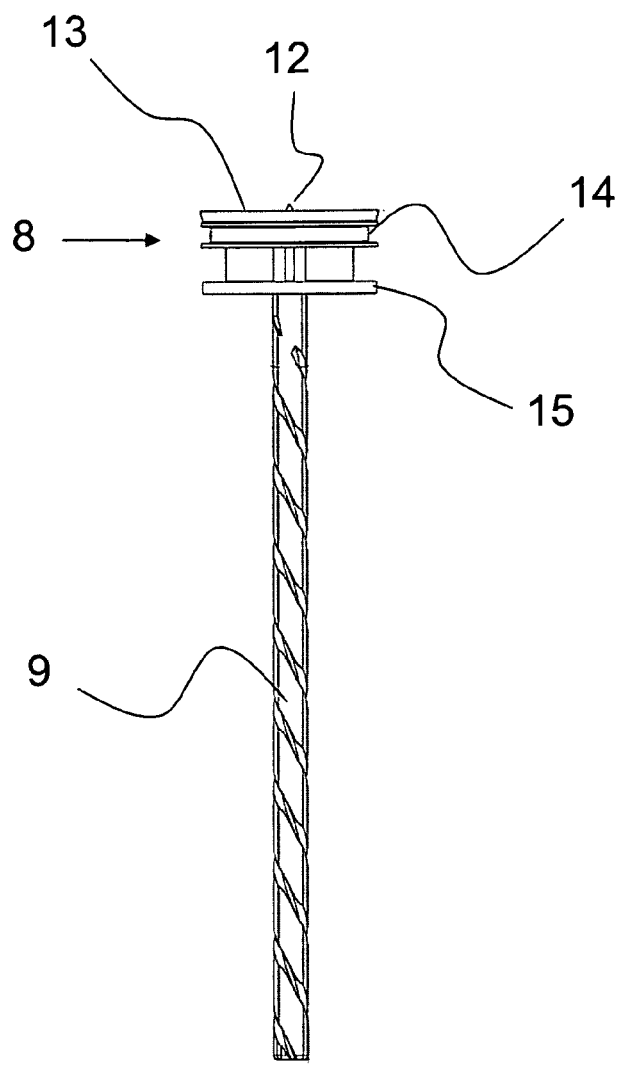
FIG. 3 is a detailed view of a piston with threaded rod.

FIG. 3 illustrates piston 8 and threaded rod 9.

Piston 8 and threaded rod 9 may be of one-piece construction formed from plastics.

Piston 8 has a spike 12 on piston head 13, which in a preferred embodiment of the invention is formed as an embedded metal part.

Piston 8 has a groove 14 which may for example serve to receive an elastomeric gasket.

Furthermore, the piston comprises a spaced guide plate 15 which reduces the risk of canting piston 8.

Threaded rod 9 has a relatively steep thread which in this exemplary embodiment has a pitch from 1.5 to 2.5 cm. Thus, piston 8 may be moved up and down in the mixing chamber with only a few rotations. At the same time it may be ensured by a suitable pitch of the thread of threaded rod 9 that the user notices when the bone cement has already solidified too much. In this case moving up the piston would be so difficult that it is recognizable when turning the rotary handle (5 in FIG. 1).

Figure 4:
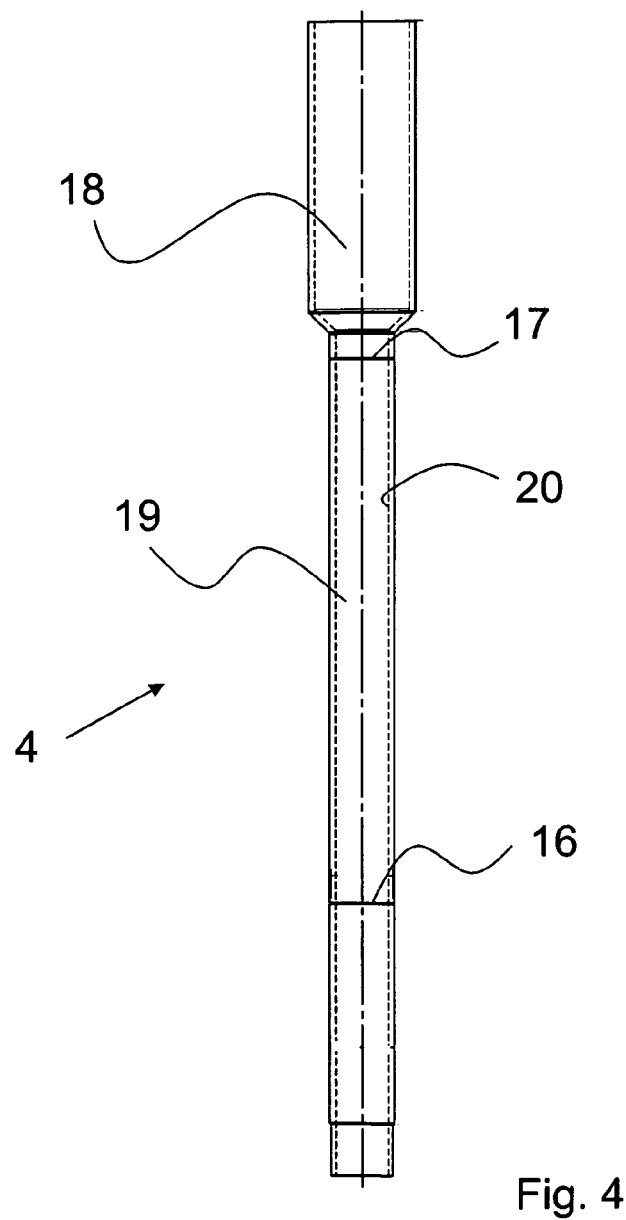
FIG. 4 shows a rod for moving the mixing paddle.

FIG. 4 shows a detailed view of rod 4 by which the mixing paddle (not shown) is moved.

The mixing paddle is attached to the lower end of rod 4, and the manipulation handle at the upper end thereof.

Rod 4 is formed as a tube into which a monomer container may be inserted.

In this exemplary embodiment, the position of the monomer container is represented by dashed line 20.

In this embodiment, the lower portion 19 of the rod has a smaller diameter than the upper portion 18 of the rod. The monomer container may for example come to rest against the collar formed between the two portions.

Tubular rod 4 has a lower predetermined breaking point 16 and an upper predetermined breaking point 17. Thus, rod 4 which at the same time serves as a transfer hose, may have a different length, depending on the application. The monomer container arranged inside rod 4, by contrast, has no predetermined breaking point but is firmly connected to manipulation handle 3 (not shown). After breaking off the manipulation handle at predetermined breaking point 16 or 17, the monomer container is pulled out from rod 4, and there are no remains of the monomer container left which could impede the exit of the mixed bone cement.

Figure 5:
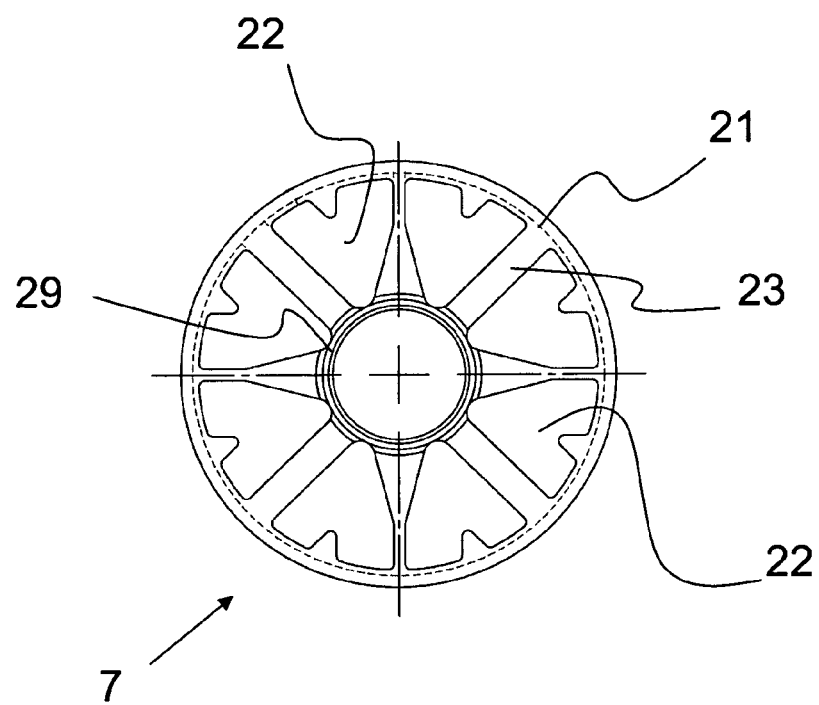
FIG. 5 shows one embodiment of a mixing paddle.

FIG. 5 schematically illustrates a mixing paddle 7.

The mixing paddle may take almost any form. In this exemplary embodiment, the mixing paddle comprises a ring 21 which is connected to an inner ring 29 by webs 23. Inner ring 29 is mounted around the actuating rod (4 in FIG. 2). Recesses 22 are formed between the webs through which the bone cement may flow back and forth past webs 23 and is mixed in this manner.

Figure 6:
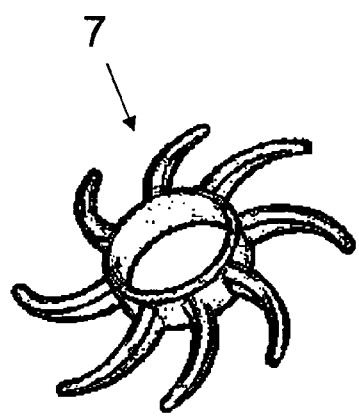
FIGS. 6 through 8 show alternative embodiments of a mixing paddle.
Figure 8:
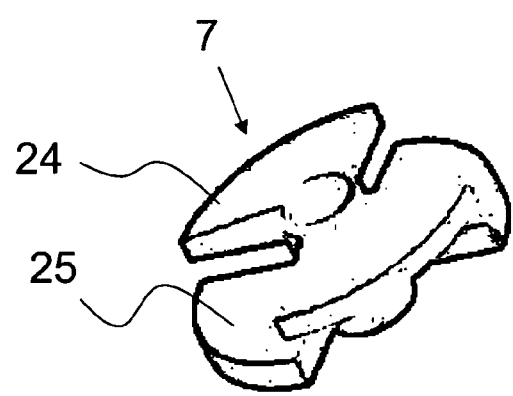
Figure 7:
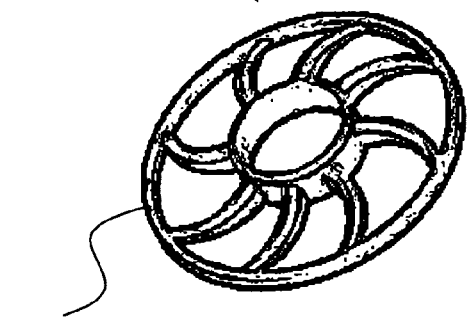

FIGS. 6 through 8 show alternative embodiments of a mixing paddle.

The mixing paddle illustrated in FIG. 6 has slanted wings to generate a turbulent flow and thus achieve better mixing.

The mixing paddle shown in FIG. 7 is formed similarly and additionally has an outer ring 21 which prevents inhomogeneously mixed residues from being formed at the wall of the mixing chamber.

FIG. 8 shows another embodiment of a mixing paddle 7 which comprises an upper 24 and a lower 25 plate. The bone cement may flow through the gaps formed between the plates. This embodiment of the invention especially permits rapid mixing of the bone cement without any rotational movement.

Figure 9:
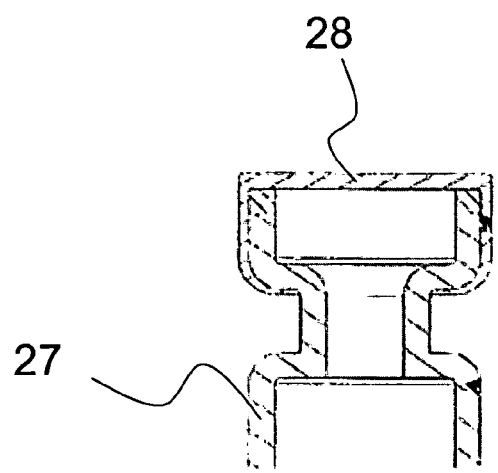
FIG. 9 illustrates a monomer container.

FIG. 9 shows a view of a detail of monomer container 27, only the head of monomer container 27 being shown in this detailed view.

The walls of container 27 may be made from plastics or aluminum. Monomer container 27 is closed by a lid 28. This may be screwed-on lid, for example, or as in this exemplary embodiment a pressed-on aluminum lid, or a plastic lid, for example made of PTFE, which engages monomer container 27 and is suitable sealed. To extract the monomer, the lid 28 may be perforated with a pointed object, for example by the spike on the piston shown in FIG. 3, whereby the monomer exits. To permit the monomer to exit from the otherwise closed monomer container 27, monomer container 27 is partially filled with a gas volume which due to the pressure difference under applied vacuum displaces the monomer (not shown).

The invention provides for particularly simple and safe mixing of bone cement.

It will be appreciated that the invention is not limited to one combination of the features described above, rather a person skilled in the art will use any features as far as reasonable in any combination.

LIST OF REFERENCE NUMERALS

1 Mixing device
2 Housing
3 Manipulation handle
4 Rod
5 Rotary handle
6 Upper housing part
7 Mixing paddle
8 Piston
9 Threaded rod
10 Mixing chamber
11 Spindle nut
12 Spike
13 Piston head
14 Groove
15 Guide plate
16 Predetermined breaking point
17 Predetermined breaking point
18 Upper portion
19 Lower portion
20 Dashed line
21 Ring
22 Recess
23 Web
24 Upper plate
25 Lower plate
27 Monomer container
28 Lid
29 Inner Ring

The invention claimed is:

1. A mixing device for bone cement, comprising:
a tubular rod, the tubular rod having a first end and a second end opposite the first end;
a manipulation handle at the first end of the tubular rod;
a monomer container situated in the tubular rod for containing a monomer, wherein the monomer container is constructed of a plastic material with a diffusion barrier layer;
a housing with a mixing chamber for containing a bone cement powder;
a mixing paddle arranged in the mixing chamber, the mixing paddle being connected with the tubular rod at the second end;
a piston in the mixing chamber that is moveable away from the mixing paddle to generate a vacuum in the mixing chamber; and
a threaded spindle that cooperates with and moves the piston,
wherein the mixing chamber takes the shape of a cylinder.

2. The mixing device as claimed in claim 1, wherein the monomer container takes the form of an insertion hose within the tubular rod.

3. The mixing device as claimed in claim 1, wherein the threaded spindle includes a rotary handle that cooperates with a threaded rod connected to the piston, and wherein rotation of the rotary handle imparts translational movement to the threaded rod and the piston.

4. The mixing device as claimed in claim 1, wherein the mixing paddle is arranged at the side of the housing opposite the piston.

5. The mixing device as claimed in claim 4, wherein the tubular rod has at least one predetermined breaking point.

6. The mixing device as claimed in claim 1, wherein the piston has a stroke that is dimensioned such that a residual pressure from 50 to 300 mbar is generated.

7. The mixing device as claimed in claim 1, wherein the piston is further movable toward the tubular rod for pressing out the bone cement.

8. The mixing device as claimed in claim 1, wherein said manipulation handle is detachable.

9. A mixing device for bone cement, comprising:
a tubular rod, the tubular rod having a first end and a second end opposite the first end;
a manipulation handle at the first end of the tubular rod;
a monomer container situated in the tubular rod for containing a monomer, wherein the monomer container is constructed of a plastic material having a diffusion barrier layer;
a housing having a mixing chamber for containing a bone cement powder;
a mixing paddle arranged in the mixing chamber, the mixing paddle being connected to the tubular rod at the second end;
a piston in the mixing chamber that is moveable away from the mixing paddle to generate a vacuum in the mixing chamber; and
a spring that is connected to and imparts movement to the piston,
wherein the mixing chamber takes the shape of a cylinder.

* * * * *